United States Patent
Saly et al.

(10) Patent No.: US 11,536,708 B2
(45) Date of Patent: Dec. 27, 2022

(54) METHODS TO FABRICATE DUAL PORE DEVICES

(71) Applicant: Applied Materials, Inc., Santa Clara, CA (US)

(72) Inventors: Mark J. Saly, Santa Clara, CA (US); Keenan Navarre Woods, San Ramon, CA (US); Joseph R. Johnson, Redwood City, CA (US); Bhaskar Jyoti Bhuyan, San Jose, CA (US); William J. Durand, Oakland, CA (US); Michael Chudzik, Mountain View, CA (US); Raghav Sreenivasan, Fremont, CA (US); Roger Quon, Rhinebeck, NY (US)

(73) Assignee: APPLIED MATERIALS, INC., Santa Clara, CA (US)

( * ) Notice: Subject to any disclaimer, the term of this patent is extended or adjusted under 35 U.S.C. 154(b) by 388 days.

(21) Appl. No.: 16/738,629

(22) Filed: Jan. 9, 2020

(65) Prior Publication Data
US 2021/0215664 A1 Jul. 15, 2021

(51) Int. Cl.
*B82Y 15/00* (2011.01)
*B82Y 40/00* (2011.01)
(Continued)

(52) U.S. Cl.
CPC ........ *G01N 33/48721* (2013.01); *B82Y 40/00* (2013.01); *C12Q 1/6869* (2013.01); *B82Y 15/00* (2013.01)

(58) Field of Classification Search
None
See application file for complete search history.

(56) References Cited

U.S. PATENT DOCUMENTS

| 8,961,763 B2 | 2/2015 | Dunbar et al. |
| 8,986,928 B2 | 3/2015 | Turner et al. |
| (Continued) | | |

FOREIGN PATENT DOCUMENTS

| CN | 104458813 A | 3/2015 |
| CN | 104730111 A | 6/2015 |
| (Continued) | | |

OTHER PUBLICATIONS

Zhang et al., "Single Molecule DNA Resensing Using a Two-Pore Device", Small 2018, 14, 1801890 (11 pages).
(Continued)

*Primary Examiner* — Robert T. Crow
(74) *Attorney, Agent, or Firm* — Patterson + Sheridan, LLP

(57) ABSTRACT

Embodiments of the present disclosure provide dual pore sensors and methods for producing these dual pore sensors. The method includes forming a film stack, where the film stack contains two silicon layers and two membrane layers, and then etching the film stack to produce a channel extending therethrough and having two reservoirs and two nanopores. The method also includes depositing a oxide layer on inner surfaces of the reservoirs and nanopores, depositing a dielectric layer on the oxide layer, and forming a metal contact extending through a portion of the stack. The method further includes etching the dielectric layers to form wells, etching the first silicon layer to reveal the protective oxide layer deposited on the inner surfaces of a reservoir, and etching the protective oxide layer deposited on the inner surfaces of the reservoirs and the nanopores.

20 Claims, 8 Drawing Sheets

(51) Int. Cl.
*G01N 33/487* (2006.01)
*B01D 67/00* (2006.01)
*C12Q 1/6869* (2018.01)

(56) References Cited

U.S. PATENT DOCUMENTS

| | | |
|---|---|---|
| 9,194,860 B2 | 11/2015 | Peng et al. |
| 9,201,057 B2 | 12/2015 | Peng et al. |
| 9,696,277 B2 | 7/2017 | Dunbar et al. |
| 9,863,912 B2 | 1/2018 | Dunbar et al. |
| 10,208,342 B2 | 2/2019 | Dunbar et al. |
| 10,794,895 B2 | 10/2020 | Xie |
| 10,908,121 B2 | 2/2021 | Yanagi |
| 2013/0233709 A1 | 9/2013 | Dunbar et al. |
| 2014/0099726 A1 | 4/2014 | Heller |
| 2014/0131202 A1 | 5/2014 | Peng et al. |
| 2014/0131203 A1 | 5/2014 | Peng et al. |
| 2014/0318964 A1 | 10/2014 | Dunbar et al. |
| 2016/0231307 A1 | 8/2016 | Xie |
| 2016/0266089 A1 | 9/2016 | Morin et al. |
| 2017/0074855 A1 | 3/2017 | Morin et al. |
| 2017/0269034 A1 | 9/2017 | Dunbar et al. |
| 2018/0304206 A1* | 10/2018 | Striemer ............ B81C 1/00119 |
| 2018/0372713 A1 | 12/2018 | Stamm et al. |
| 2019/0094180 A1 | 3/2019 | Yanagi |
| 2019/0383806 A9 | 12/2019 | Morin et al. |
| 2020/0150084 A1 | 5/2020 | Dunbar et al. |
| 2020/0393456 A1 | 12/2020 | Alexandrakis et al. |
| 2020/0400648 A1 | 12/2020 | Xie |
| 2020/0400649 A1 | 12/2020 | Xie |

FOREIGN PATENT DOCUMENTS

| | | |
|---|---|---|
| WO | 2016127007 A2 | 8/2016 |
| WO | 2017165267 A1 | 9/2017 |
| WO | 2019118495 A1 | 6/2019 |

OTHER PUBLICATIONS

Liu et al., "Controlling DNA Tug-of-War in a Dual Nanopore Device", Dept. of Physics, McGill University, Montreal, QC, Canada; arXiv:1811.11105v1, Nov. 2018, (33 pages).

Maitra et al., "Recent advances in nanopore sequencing", NIH Public Access, Electrophoresis. Dec. 2012; 33 (23): 3418-3428. doi: 10.1002/elps.201 200272 (11 pages).

International Search Report and Written Opinion dated Mar. 30, 2021 for Application No. PCT/US2020/063309.

King, Sean et al., "Intrinsic stress eflecton fracture toughness of plasma enhanced chemical vapor deposited SiNx: H films", Thin Solid Films, 2010, vol. 518, No. 17, pp. 4898-4907.

Ma, Hong-Ping et al., "Measurements of microstructural, chemical, optical, and electrical properties of silicon-oxygen-nitrogen films prepared by plasma-enhanced atomic layer deposition", Nanomaterials, 2018, vol. 8, No. 12, inner pp. 1-14.

International Search Report and Written Report dated Sep. 29, 2021 for Application No. PCT/US2021/036523.

* cited by examiner

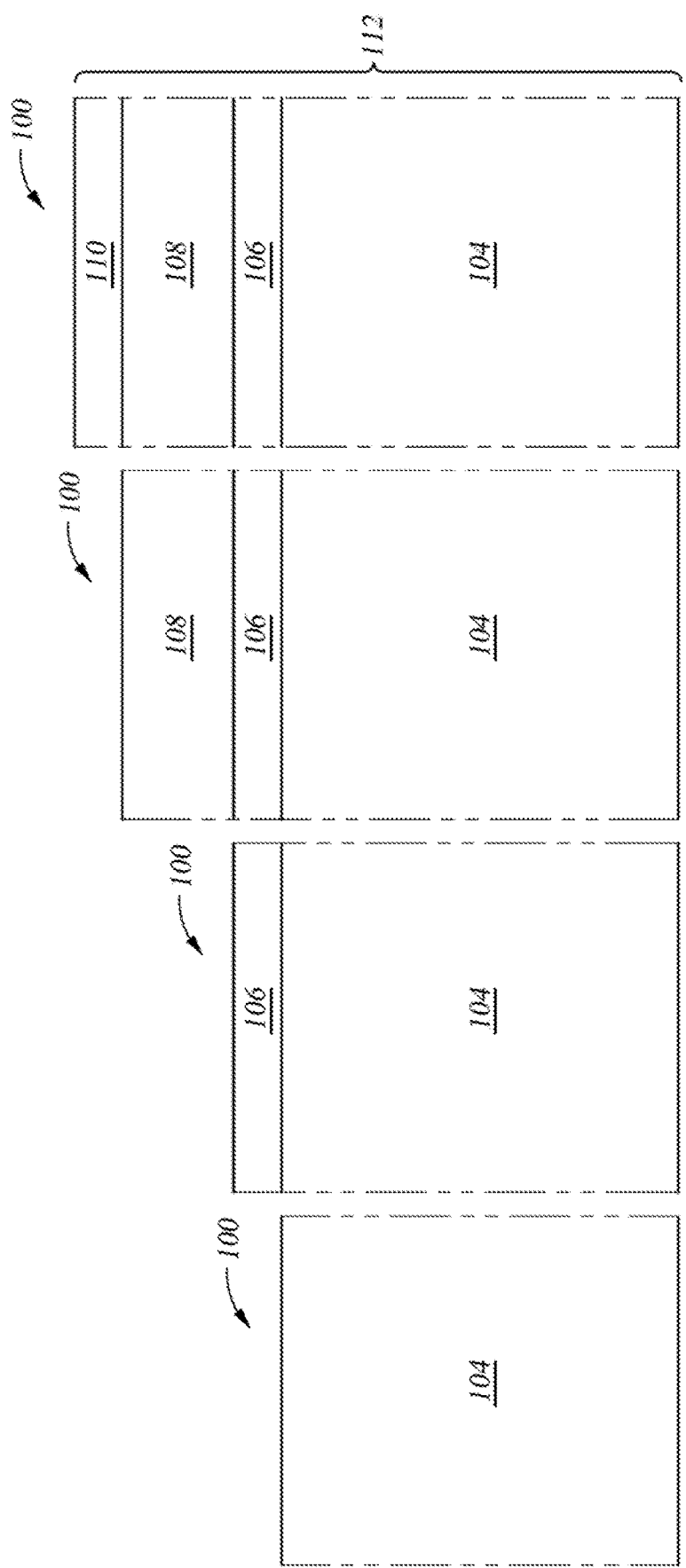

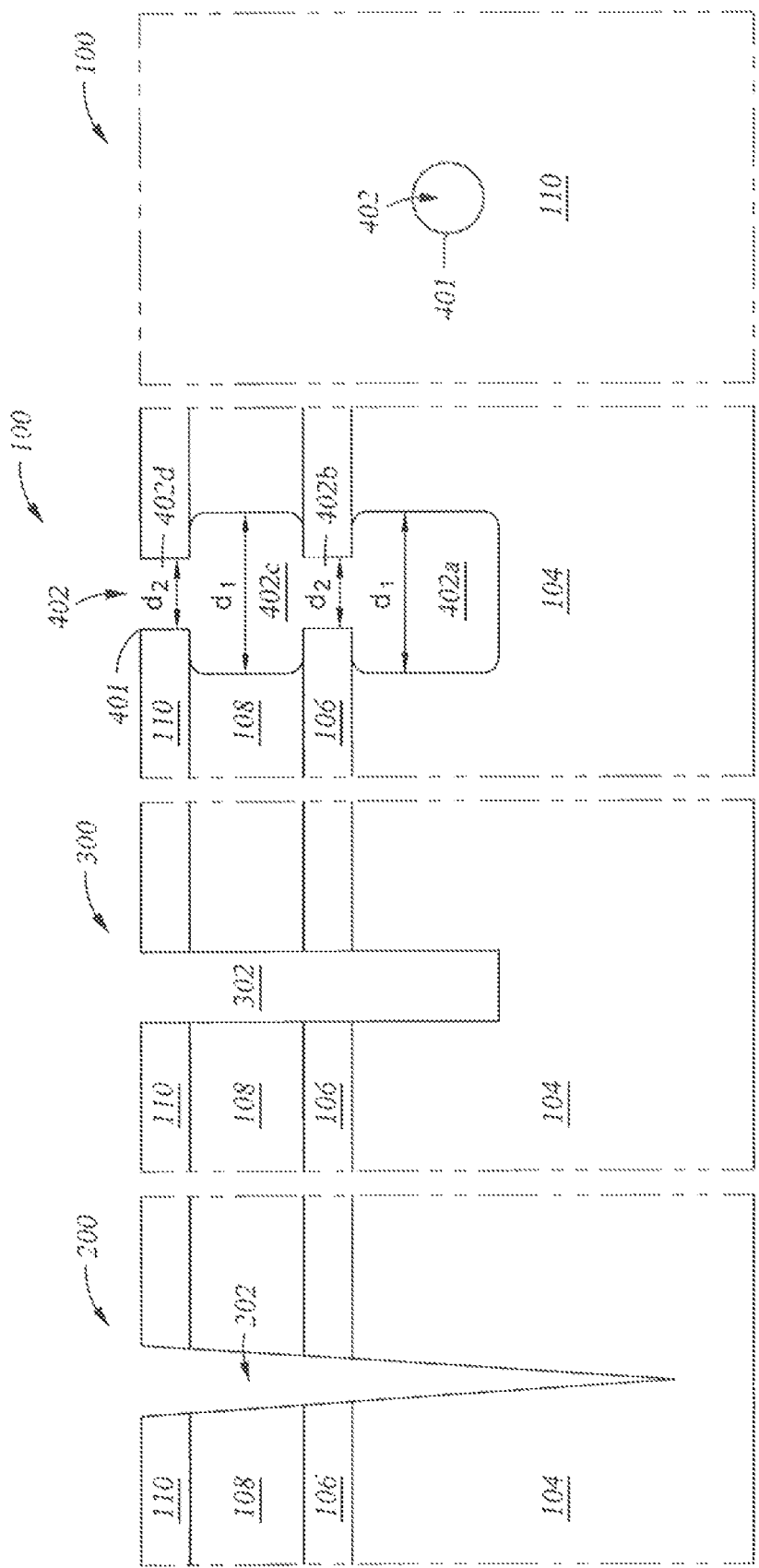

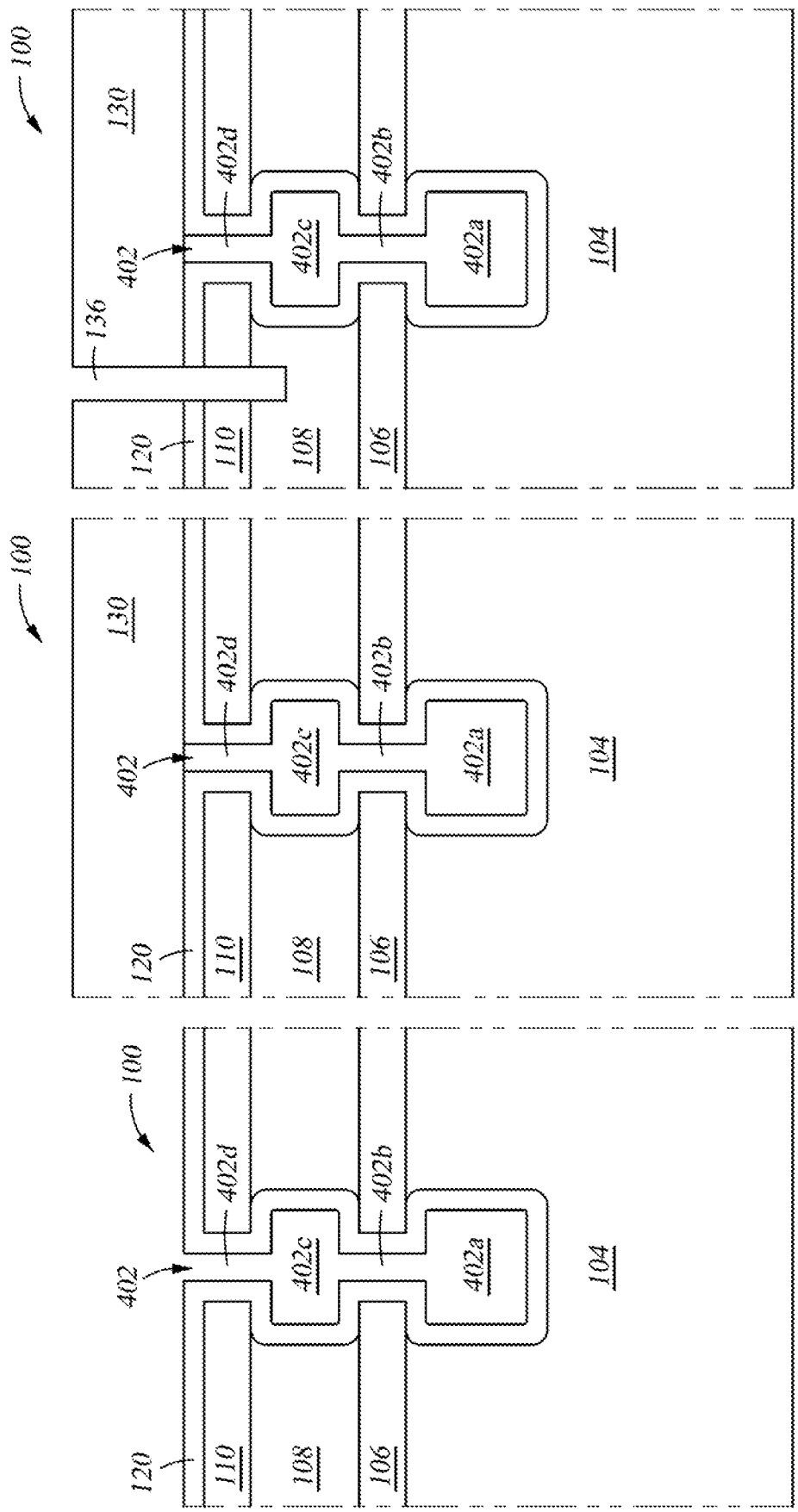

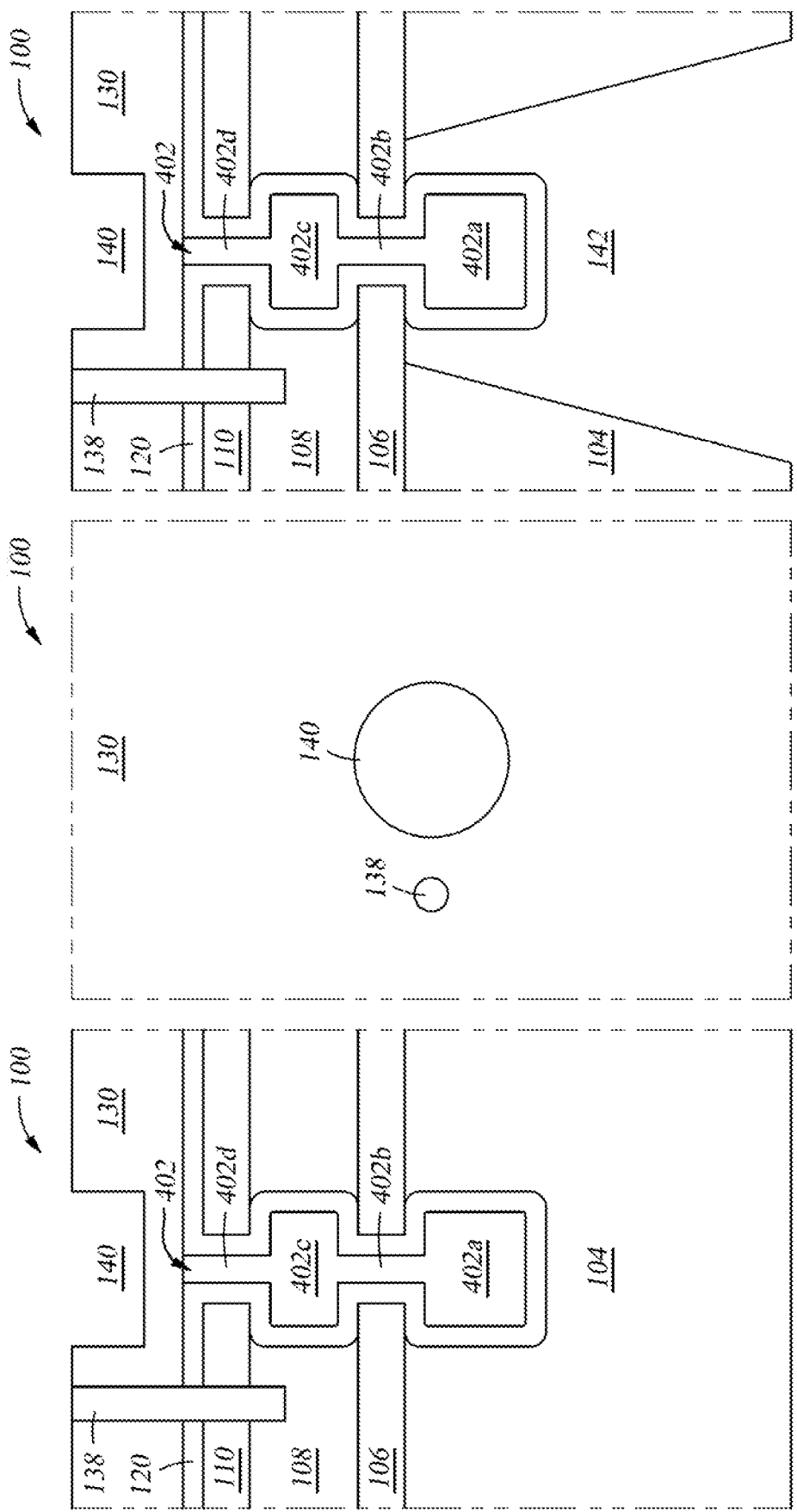

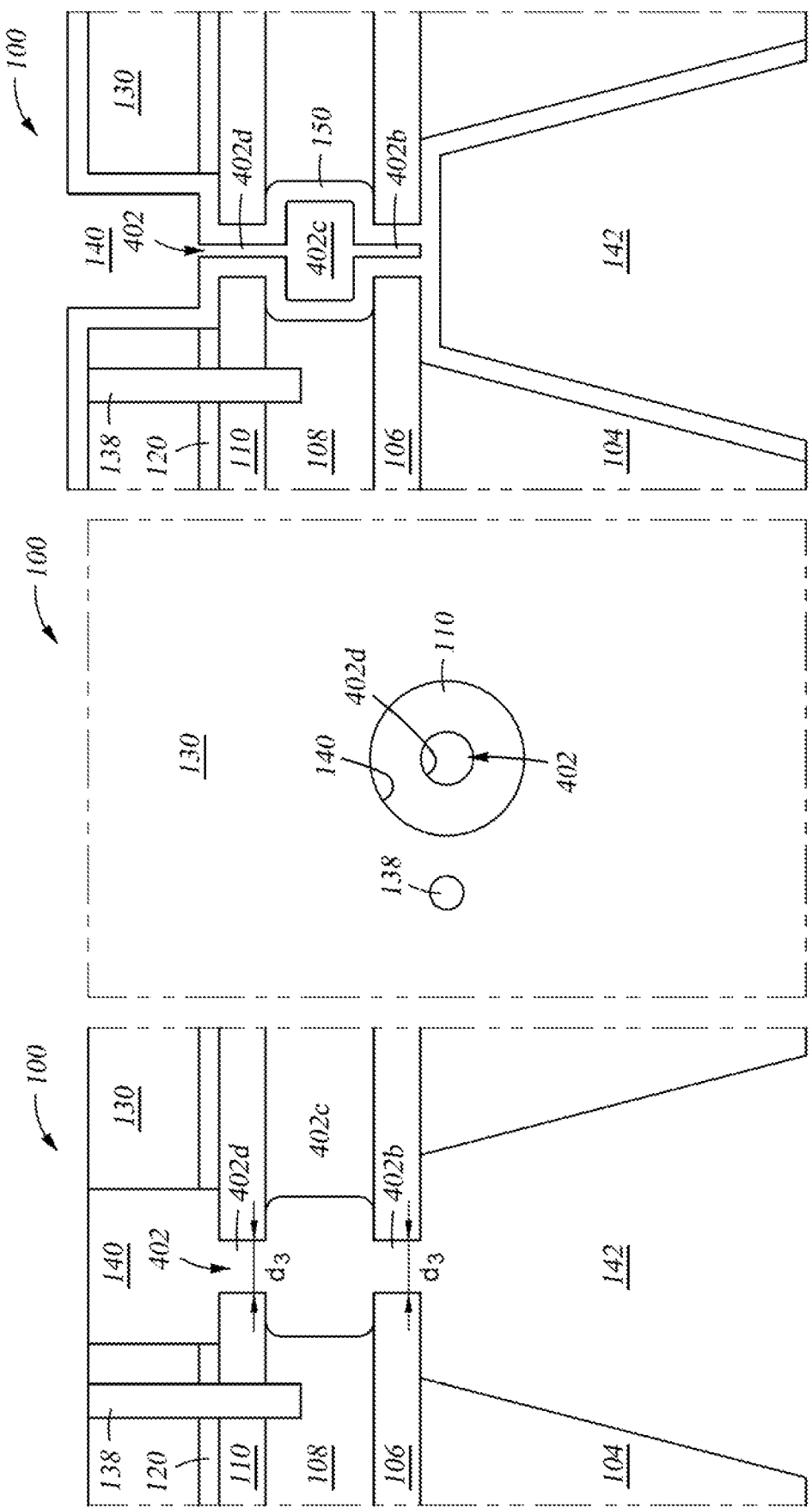

METHODS TO FABRICATE DUAL PORE DEVICES

BACKGROUND

Field

Embodiments herein relate to flow cells to be used with solid-state nanopore sensors and methods of manufacturing such flow cells.

Description of the Related Art

Solid-state nanopore sensors have emerged as a low-cost, easily transportable, and rapid processing biopolymer, e.g., DNA or RNA, sequencing technology. Solid-state nanopore sequencing of a biopolymer strand typically incudes translocating a biopolymer strand through one or more nanoscale sized openings (e.g., nanopore) each having a diameter of about 100 nm. In a single pore sensor, a nanopore is disposed through a membrane layer which separates two conductive fluid reservoirs. The biopolymer strand to be sequenced, e.g., a characteristically negatively charged DNA or RNA strand, is introduced into one of the two conductive fluid reservoirs and is then drawn through the nanopore by providing an electric potential therebetween. As the biopolymer strand travels through the nanopore the different monomer units thereof, e.g., protein bases of a DNA or RNA strand, occlude different percentages of the nanopore thus changing the ionic current flow therethrough. The resulting current signal pattern can be used to determine the sequence of monomer units in the biopolymer strand, such as the sequence of proteins in a DNA or RNA strand. Generally, single pore sensors lack a mechanism for slowing the rate of translocation of the biopolymer strand through the nanopore while still providing sufficient electrical potential between the two reservoirs to optimize the signal to noise ratio in the resulting current signal pattern.

Beneficially, dual pore sensors provide a mechanism for controlling the rate of translocation of a biopolymer strand by co-capturing the biopolymer strand in the two nanopores thereof. A typical dual pore sensor features two fluid reservoirs side-by-side separated by a wall, a common fluid chamber, and a membrane separating the common fluid chamber from each of the fluid reservoirs, the membrane layer having the two nanopores disposed therethrough. A biopolymer strand to be sequenced travels from the first fluid reservoir to the common chamber and from the common chamber to the second fluid reservoir through a second nanopore. Desirably the two nanopores are positioned close enough to one another to allow for co-capture of the biopolymer strand. When the biopolymer strand is co-captured by both of the nanopores, competing electric potentials are applied across each of the nanopores to create a "tug-of-war" where the opposite ends of the biopolymer strand are pulled in opposite directions of travel. Beneficially, the difference between the competing electric potentials can be adjusted to control the rate of translocation of the biopolymer strand through the nanopores and thus the resolution of the electrical signal current signal pattern or patterns resulting therefrom.

The known manufacturing methods for dual pore sensors are generally relatively small scale and therefore incompatible with the high volume manufacturing, quality, repeatability, and cost requirements needed to move dual pore sensors into the public market. Further, the known manufacturing methods generally limit the minimum spacing between the two nanopores to about 500 nm which thus limits the ability of dual pore sensors formed therefrom to sequence relativity shorter biopolymer strands.

Accordingly, there is a need for improved dual pore sensors and methods for forming the same.

SUMMARY

Embodiments of the present disclosure provide solid state, vertically aligned, dual pore sensors which may be used for biomolecule sequencing, such as DNA, RNA, and/or other biopolymers, as well as for methods of manufacturing these dual pore sensors.

In one or more embodiments, a method of forming a dual pore sensor is provided and includes forming a film stack, where the film stack contains a first silicon layer, a first membrane layer disposed on the first silicon layer, a second silicon layer disposed on the first membrane layer, and a second membrane layer disposed on the second silicon layer, and then etching the film stack to produce a first reservoir in the first silicon layer, a first nanopore in the first membrane layer, a second reservoir in the second silicon layer, a second nanopore in the second membrane layer, and a channel and in fluid communication with the first and second reservoirs and the first and second nanopores. The method also includes depositing a protective oxide layer on the second membrane layer and inner surfaces of the first and second reservoirs and inner surfaces of the first and second nanopores, depositing a dielectric layer on the protective oxide layer disposed on the second membrane layer and covering the second nanopore, and forming a metal contact which extends through the dielectric layer, the protective oxide layer, and the second membrane layer, and at least partially into the second silicon layer. The method further includes etching at least a portion of the dielectric layer to form a well above the second nanopore, etching at least a portion of the first silicon layer to reveal at least a portion of the protective oxide layer deposited on the inner surfaces of the first reservoir, and etching the protective oxide layer deposited on the inner surfaces of the first and second reservoirs and the inner surfaces of the first and second nanopores.

In other embodiments, a method of forming a dual pore sensor is provided and includes forming a film stack, where the film stack contains a first silicon layer, a first membrane layer disposed on the first silicon layer, a second silicon layer disposed on the first membrane layer, a second membrane layer disposed on the second silicon layer, a first reservoir in the first silicon layer, a first nanopore in the first membrane layer, a second reservoir in the second silicon layer, a second nanopore in the second membrane layer, and a channel and in fluid communication with the first and second reservoirs and the first and second nanopores. The method also includes depositing a protective oxide layer on the second membrane layer and inner surfaces of the first and second reservoirs and inner surfaces of the first and second nanopores, depositing a dielectric layer on the protective oxide layer disposed on the second membrane layer and covering the second nanopore, forming a metal contact which extends through the dielectric layer, the protective oxide layer, and the second membrane layer, and at least partially into the second silicon layer. The method further includes etching at least a portion of the dielectric layer to form a well above the second nanopore, etching at least a portion of the first silicon layer to reveal at least a portion of the protective oxide layer deposited on the inner surfaces of the first reservoir, etching the protective oxide layer deposited on the inner surfaces of the first and second reservoirs and the inner surfaces of the first and second nanopores, and depositing a spacer layer on at least the inner surfaces of the first and second nanopores.

In some embodiments, a dual pore sensor is provided and contains a film stack which contains a first silicon layer, a first membrane layer disposed on the first silicon layer, a second silicon layer disposed on the first membrane layer, a second membrane layer disposed on the second silicon layer, a first reservoir in the first silicon layer, a first nanopore in the first membrane layer, a second reservoir in the second silicon layer, a second nanopore in the second membrane layer, and a channel and in fluid communication with the first and second reservoirs and the first and second nanopores, where each of the first nanopore and the second nanopore has a diameter of about 1 nm to about 50 nm. The dual pore sensor also contains a well formed in a dielectric layer disposed above the second membrane layer and a metal contact extending through the dielectric layer, the second membrane layer, and into the second silicon layer.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only typical embodiments of this disclosure and are therefore not to be considered limiting of its scope, for the disclosure may admit to other equally effective embodiments.

FIGS. 1A-1D depict schematic cross-sectional views of a workpiece during different stages of forming a film stack, according to one or more embodiments described and discussed herein.

FIG. 2 depicts a schematic cross-sectional view of a workpiece containing a film stack having a channel formed by a process, according to one or more embodiments described and discussed herein.

FIG. 3 depicts a schematic cross-sectional view of a workpiece containing a film stack having a channel formed by another process, according to one or more embodiments described and discussed herein.

FIG. 4A depicts a schematic cross-sectional view of a workpiece containing a film stack having a channel formed by another process, according to one or more embodiments described and discussed herein.

FIG. 4B depicts a schematic top view of the workpiece depicted in FIG. 4A, according to one or more embodiments described and discussed herein.

FIG. 5 depicts a schematic cross-sectional view of the workpiece depicted in FIG. 4A after being exposed to a deposition process, according to one or more embodiments described and discussed herein.

FIG. 6 depicts a schematic cross-sectional view of the workpiece depicted in FIG. 5 after being exposed to another deposition process, according to one or more embodiments described and discussed herein.

FIG. 7 depicts a schematic cross-sectional view of the workpiece depicted in FIG. 6 after being exposed to an etch process, according to one or more embodiments described and discussed herein.

FIG. 10A depicts a schematic cross-sectional view of the workpiece depicted in FIG. 9 after being exposed to another etch process, according to one or more embodiments described and discussed herein.

FIG. 10B depicts a schematic top view of the workpiece depicted in FIG. 10A, according to one or more embodiments described and discussed herein.

FIG. 11 depicts a schematic cross-sectional view of the workpiece depicted in FIG. 10A after being exposed to another etch process, according to one or more embodiments described and discussed herein.

FIG. 12A depicts a schematic cross-sectional view of the workpiece depicted in FIG. 11A after being exposed to another etch process, according to one or more embodiments described and discussed herein.

FIG. 12B depicts a schematic top view of the workpiece depicted in FIG. 12A, according to one or more embodiments described and discussed herein.

FIG. 13 depicts a schematic cross-sectional view of the workpiece depicted in FIG. 12A after being exposed to a deposition process, according to one or more embodiments described and discussed herein.

To facilitate understanding, identical reference numerals have been used, where possible, to designate identical elements that are common to the Figures. It is contemplated that elements and features of one or more embodiments may be beneficially incorporated in other embodiments.

DETAILED DESCRIPTION

Figure 9:
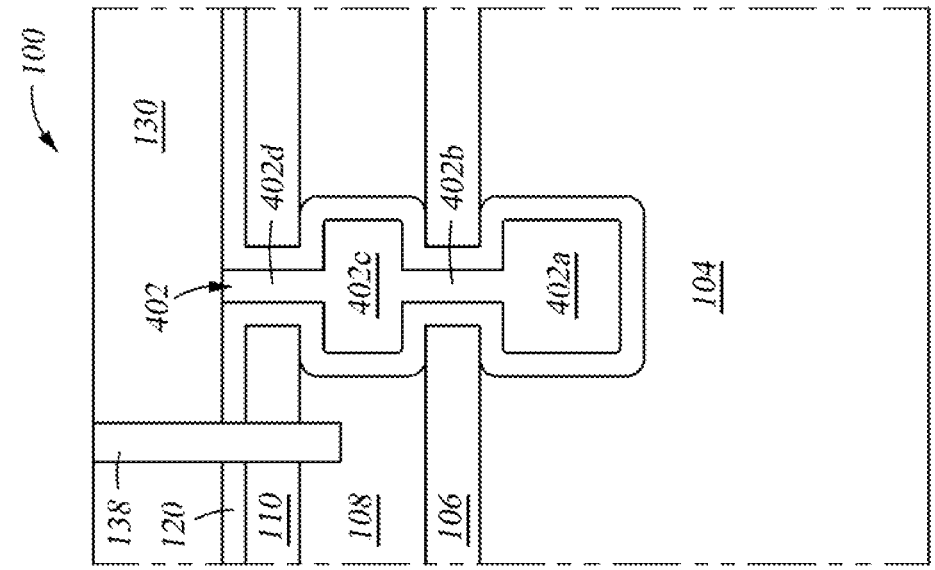
FIG. 9 depicts a schematic cross-sectional view of the workpiece depicted in FIG. 8 after being exposed to another etch process, according to one or more embodiments described and discussed herein.

Embodiments of the present disclosure provide solid state dual pore sensors which may be used for biopolymer sequencing, and methods of manufacturing the same. Generally, the dual pore sensors described and discussed herein are formed by electronics manufacturing techniques which include combinations of multiple processes for deposition, lithography, and etching. The dual pore sensors include at least two fluid reservoirs which are disposed one above the other such that the fluid reservoirs are vertically aligned with one another.

FIGS. 1A-1D depict schematic cross-sectional views of a workpiece 100 during different stages of forming a film stack 112, according to one or more embodiments. The film stack 112 is the starting structure to form dual pore sensors as described and discussed herein. The film stack 112 contains two or more silicon layers 104, 108 and two or more membrane layers 106, 110 disposed on one another as illustrated in FIG. 1D. In one or more embodiments, a first silicon layer 104 is a substrate or wafer (FIG. 1A), a first membrane layer 106 is deposited, grown, or otherwise disposed on the first silicon layer 104 (FIG. 1B), a second silicon layer 108 is deposited, grown, or otherwise disposed on the first membrane layer 106 (FIG. 1C), and a second membrane layer 110 is deposited, grown, or otherwise disposed on the second silicon layer 108 (FIG. 1D).

Each of the silicon layers 104, 108 can independently be or include one or more silicon-containing materials. Typically, each of the silicon layers 104, 108 can independently be or include amorphous silicon (α-Si) or dopant variations thereof. Each of the silicon layers 104, 108 can independently be deposited or otherwise formed by one or more deposition or coating processes, such as one or vapor deposition process, one or spin-on coatings, or other techniques. Exemplary vapor deposition processes can be or include chemical vapor deposition (CVD) or plasma-enhanced CVD (PE-CVD). In one or more examples, the first silicon layer 104 can have the same thickness or a greater thickness as the second silicon layer 108.

In one or more embodiments, the silicon layer 104 can be or include a substrate which can be any type of substrate useful for forming the dual pore sensors described and discussed herein. Exemplary substrates can be or include those commonly used in semiconductor device manufacturing, such as an N-type or P-type doped monocrystalline silicon wafers, or substrates formed undoped monocrystalline silicon, e.g., intrinsic monocrystalline silicon wafers. In some embodiments, the silicon layer 104 is a doped or undoped silicon substrate or wafer having an epitaxial layer of undoped monocrystalline silicon formed thereon. In other embodiments, the silicon layer 104 features a layered stack of silicon, an electrically insulating material, such as sapphire or a silicon oxide, and silicon, commonly known as a silicon-on-insulator (SOI) substrate or an SOI wafer. When used as the silicon layer 104, undoped silicon substrates, undoped silicon epitaxial layers, and SOI substrates beneficially reduce undesirable parasitic capacitance in a dual pore sensor formed therefrom when compared to a sensor formed of a doped silicon substrate.

The first silicon layer 104 can have a thickness of about 200 µm, about 250 µm, about 300 µm, about 400 µm, or about 500 µm to about 600 µm, about 650 µm, about 700 µm, about 750 µm, about 775 µm, about 800 µm, about 850 µm, about 900 µm, about 1,000 µm, about 1,200 µm, about 1,350 µm, about 1,500 µm, about 1,650 µm, about 1,800 µm, or greater. For example, the first silicon layer 104 can have a thickness of about 200 µm to about 1,800 µm, about 200 µm to about 1,650 µm, about 200 µm to about 1,500 µm, about 200 µm to about 1,000 µm, about 200 µm to about 850 µm, about 200 µm to about 800 µm, about 200 µm to about 750 µm, about 200 µm to about 700 µm, about 200 µm to about 600 µm, about 200 µm to about 500 µm, about 200 µm to about 350 µm, about 500 µm to about 1,800 µm, about 500 µm to about 1,650 µm, about 500 µm to about 1,500 µm, about 500 µm to about 1,000 µm, about 500 µm to about 850 µm, about 500 µm to about 800 µm, about 500 µm to about 775 µm, about 500 µm to about 750 µm, about 500 µm to about 700 µm, about 500 µm to about 600 µm, about 750 µm to about 1,800 µm, about 750 µm to about 1,650 µm, about 750 µm to about 1,500 µm, about 750 µm to about 1,000 µm, about 750 µm to about 850 µm, about 750 µm to about 800 µm, or about 750 µm to about 775 µm. In one or more examples, the first silicon layer 104 is a silicon-containing wafer or a silicon-containing substrate and has a thickness of about 700 µm to about 900 µm, about 725 µm to about 825 µm, or about 750 µm to about 800 µm, such as about 775 µm.

The second silicon layer 108 can have a thickness of about 10 nm, about 20 nm, about 30 nm, about 40 nm, or about 50 nm to about 60 nm, about 70 nm, about 80 nm, about 90 nm, about 100 nm, about 110 nm, about 120 nm, about 150 nm, or about 200 nm. For example, the second silicon layer 108 can have a thickness of about 10 nm to about 200 nm, about 20 nm to about 200 nm, about 20 nm to about 150 nm, about 20 nm to about 120 nm, about 20 nm to about 100 nm, about 20 nm to about 80 nm, about 20 nm to about 50 nm, about 40 nm to about 200 nm, about 40 nm to about 150 nm, about 40 nm to about 120 nm, about 40 nm to about 100 nm, about 40 nm to about 80 nm, about 40 nm to about 50 nm, about 60 nm to about 200 nm, about 60 nm to about 150 nm, about 60 nm to about 120 nm, about 60 nm to about 100 nm, or about 60 nm to about 80 nm.

Each of the membrane layers 106, 110 can independently be or include one or more silicon nitride materials. Typically, each of the membrane layers 106, 110 can independently be or include silicon nitride ($Si_3N_4$ or SiN) or dopant variations thereof. Each of the membrane layers 106, 110 can independently be deposited or otherwise formed by one or more vapor deposition processes. Exemplary vapor deposition processes can be or include CVD, PE-CVD, pulsed-CVD, atomic layer deposition (ALD), plasma-enhanced ALD (PE-ALD), physical vapor deposition (PVD), other sputtering techniques, or any combination thereof. In one or more examples, the first membrane layer 106 and the second membrane layer 110 have the same thickness or substantially the same thickness as one another.

Each of the first membrane layer 106 and the second membrane layer 110 can independently have a thickness of about 0.1 nm, about 0.2 nm, about 0.3 nm, about 0.4 nm, about 0.5 nm, about 0.6 nm, about 0.7 nm, about 0.8 nm, about 0.9 nm, about 1 nm, about 1.1 nm, about 1.2 nm, about 1.3 nm, about 1.4 nm, about 1.5 nm, about 1.6 nm, about 1.8 nm, about 2 nm, about 2.5 nm, about 3 nm, about 5 nm, about 7 nm, about 9 nm, about 10 nm, about 15 nm, about 20 nm, about 25 nm, about 30 nm, about 35 nm, about 40 nm, or greater. For example, each of the first membrane layer 106 and the second membrane layer 110 can independently have a thickness of about 0.1 nm to about 40 nm, about 0.1 nm to about 30 nm, about 0.1 nm to about 20 nm, about 0.1 nm to about 10 nm, about 0.1 nm to about 8 nm, about 0.1 nm to about 6 nm, about 0.1 nm to about 5 nm, about 0.1 nm to about 3 nm, about 0.1 nm to about 2 nm, about 0.1 nm to about 1.5 nm, about 0.1 nm to about 1.2 nm, about 0.1 nm to about 1 nm, about 0.1 nm to about 0.8 nm, about 0.1 nm to about 0.6 nm, about 0.1 nm to about 0.5 nm, about 0.1 nm to about 0.3 nm, about 0.5 nm to about 40 nm, about 0.5 nm to about 30 nm, about 0.5 nm to about 20 nm, about 0.5 nm to about 10 nm, about 0.5 nm to about 8 nm, about 0.5 nm to about 6 nm, about 0.5 nm to about 5 nm, about 0.5 nm to about 3 nm, about 0.5 nm to about 2 nm, about 0.5 nm to about 1.5 nm, about 0.5 nm to about 1.2 nm, about 0.5 nm to about 1 nm, about 0.5 nm to about 0.8 nm, about 0.5 nm to about 0.6 nm, about 0.8 nm to about 40 nm, about 0.8 nm to about 30 nm, about 0.8 nm to about 20 nm, about 0.8 nm to about 10 nm, about 0.8 nm to about 8 nm, about 0.8 nm to about 6 nm, about 0.8 nm to about 5 nm, about 0.8 nm to about 3 nm, about 0.8 nm to about 2 nm, about 0.8 nm to about 1.5 nm, about 0.8 nm to about 1.2 nm, or about 0.8 nm to about 1 nm.

FIG. 2 depicts a schematic cross-sectional view of a workpiece 200 containing the film stack 112 having a channel 202 formed therein, according to one or more embodiments described and discussed herein. The workpiece 200 can be formed from the workpiece 100 in FIG. 1D. The film stack 112 is exposed to a lithography process followed by an etching process to produce the channel 202 which extends through the second membrane layer 110, the second silicon layer 108, the first membrane layer 106, and into the first silicon layer 104. In some examples, the etching process is a reactive-ion etching (RIE) process.

The channel 202 can have a taper geometry, such that the channel 202 passing through the second membrane layer 110 has a greater diameter than the channel 202 passing through the first membrane layer 106. Each of the diameter of the pore formed in the first membrane layer 106 and the diameter of the pore formed in the second membrane layer 110 is independently determined by controlling the angle of the taper and/or length of the channel 202. These pores can have a diameter of about 1 nm, about 2 nm, or about 5 nm to about 10 nm, about 20 nm, about 30 nm, about 35 nm, about 40 nm, or about 50 nm. These pore diameters can be reduced in later process stages further described and discussed below.

FIG. 3 depicts a schematic cross-sectional view of a workpiece 300 containing the film stack 112 having a channel 302 formed therein, according to one or more embodiments described and discussed herein. The workpiece 300 can be formed or otherwise produced in two or more stages starting with the workpiece 100 in FIG. 1B. For example, the channel 302 can be formed by a litho-etch-litho-etch (LELE) process. Starting with the workpiece 100 (as depicted FIG. 1B), the first membrane layer 106 and the first silicon layer 104 are exposed to a lithography process followed by an etching process to produce the lower portion of the channel 302. Thereafter, the second silicon layer 108 is deposited on the first membrane layer 106 and the second membrane layer 110 is deposited on the second silicon layer 108. Subsequently, the second membrane layer 110 and the second silicon layer 108 are exposed to a lithography process followed by an etching process to produce the upper portion of the channel 302 (as depicted in FIG. 3). The channel 302 extends through the second membrane layer 110, the second silicon layer 108, the first membrane layer 106, and into the first silicon layer 104.

The channel 302 can have a straight-walled geometry, such that the channel 302 passing through the second membrane layer 110 has the same diameter as the channel 302 passing through the first membrane layer 106. Each of the diameter of the pore formed in the first membrane layer 106 and the diameter of the pore formed in the second membrane layer 110 is independently determined by each etching process. These pores can have a diameter of about 1 nm, about 2 nm, or about 5 nm to about 10 nm, about 20 nm, about 30 nm, about 35 nm, about 40 nm, or about 50 nm. These pore diameters can be reduced in later process stages further described and discussed below.

FIG. 4A depicts a schematic cross-sectional view of the workpiece 100 containing the film stack 112 having a channel 402 formed therein, and FIG. 4B depicts a schematic top view of the workpiece 100 depicted in FIG. 4A, according to one or more embodiments described and discussed herein. The channel 402 extends from an opening 401 on the second membrane layer 110, through the second membrane layer 110, the second silicon layer 108, the first membrane layer 106, and into the first silicon layer 104. The film stack 112 is etched to produce a first reservoir 402a in the first silicon layer 104, a first nanopore 402b in the first membrane layer 106, a second reservoir 402c in the second silicon layer 108, and a second nanopore 402d in the second membrane layer 110. The channel 402 contains the first and second reservoirs 402a, 402c and the first and second nanopores 402b, 402d, as such, the channel 402 is in fluid communication with the first and second reservoirs 402a, 402c and the first and second nanopores 402b, 402d.

The workpiece 100, as depicted FIG. 1D, is exposed to an etch process, such as a plasma etch process, to produce the channel 402 including the first and second reservoirs 402a, 402c and the first and second nanopores 402b, 402d. In one or more embodiments, the material can be removed to form the channel 402 by using a plasma-based dry etch process. For example, the second membrane layer 110, the second silicon layer 108, the first membrane layer 106, and the first silicon layer 104 can be sequentially exposed to the plasma containing activated radical species of one or more etchants, such as the radial species of one or more halogen-containing gases. Exemplary etchants can be or include one or more of fluorine, hydrogen fluoride, chlorine, hydrogen chloride, or any combinations thereof. An exemplary system which may be used to remove the material to for the channel 402 is the Producer® Selectra® Etch system, commercially available from Applied Materials, Inc., of Santa Clara, Calif. as well as suitable systems from other manufacturers.

In one or more embodiments, the first and second reservoirs 402a, 402c can have the same diameter, $d_1$, as each other and the first and second nanopores 402b, 402d can have the same diameter, $d_2$, as each other. In other embodiments, not shown, the first and second reservoirs 402a, 402c can independently have different diameters as each other and the first and second nanopores 402b, 402d can independently have different diameters as each other. The diameters of the first and second nanopores 402b, 402d can be reduced in later process stages further described and discussed below.

Each of the first and second reservoirs 402a, 402c can independently have diameter $d_1$ of about 200 nm, about 300 nm, about 400 nm, or about 450 nm to about 500 nm, about 550 nm, about 600 nm, about 700 nm, about 800 nm, or about 1,000 nm. For example, each of the first and second reservoirs 402a, 402c can independently have diameter $d_1$ of about 200 nm to about 800 nm, about 200 nm to about 600 nm, about 200 nm to about 500 nm, about 200 nm to about 400 nm, about 400 nm to about 800 nm, about 400 nm to about 600 nm, about 400 nm to about 500 nm, about 450 nm to about 500 nm, about 500 nm to about 800 nm, about 500 nm to about 600 nm, or about 500 nm to about 550 nm.

Each of the first and second nanopores 402b, 402d can independently have diameter $d_2$ of about 1 nm, about 2 nm, or about 5 nm to about 10 nm, about 20 nm, about 30 nm, about 35 nm, about 40 nm, about 50 nm, about 60 nm, or about 80 nm. For example, each of the first and second nanopores 402b, 402d can independently have diameter $d_2$ of about 1 nm to about 80 nm, about 1 nm to about 60 nm, about 1 nm to about 50 nm, about 1 nm to about 40 nm, about 1 nm to about 35 nm, about 1 nm to about 30 nm, about 1 nm to about 25 nm, about 1 nm to about 20 nm, about 1 nm to about 10 nm, about 10 nm to about 80 nm, about 10 nm to about 60 nm, about 10 nm to about 50 nm, about 10 nm to about 40 nm, about 10 nm to about 35 nm, about 10 nm to about 30 nm, about 10 nm to about 25 nm, about 10 nm to about 20 nm, about 10 nm to about 15 nm, about 20 nm to about 80 nm, about 20 nm to about 60 nm, about 20 nm to about 50 nm, about 20 nm to about 40 nm, about 20 nm to about 35 nm, about 20 nm to about 30 nm, or about 20 nm to about 25 nm.

FIG. 5 depicts a schematic cross-sectional view of the workpiece 100 containing a protective oxide layer 120 deposited or otherwise formed on the upper surface of the second membrane layer 110 as well as the inner surfaces of the channel 402, such as the inner surfaces of the first and second reservoirs 402a, 402c and the inner surfaces of the first and second nanopores 402b, 402d. The protective oxide layer 120 is a protective coating for the inner wall formed by the channel 402. The protective oxide layer 120 can be or include one or more dielectric materials, such as silicon oxide, one or more metal oxides, one or more metal silicates, dopants thereof, or any combination thereof. For example, the protective oxide layer 120 can be or include silicon oxide, aluminum oxide, yttrium oxide, hafnium oxide, zirconium oxide, titanium oxide, tantalum oxide, aluminum silicate, yttrium silicate, hafnium silicate, zirconium silicate, titanium silicate, tantalum silicate, or any combination thereof.

In some embodiments, the workpiece 100 depicted in FIG. 4A is exposed to one or more deposition processes, such as vapor deposition processes, to form or otherwise deposit the protective oxide layer 120. Exemplary vapor deposition processes used to form or otherwise deposit the protective oxide layer 120 can be or include ALD, PE-ALD, CVD, PE-CVD, pulsed-CVD, or any combination thereof. In one or more examples, the protective oxide layer 120 is deposited by an ALD process or a PE-ALD process. The protective oxide layer 120 has a thickness of about 0.5 nm, about 1 nm, about 2 nm, about 3 nm, about 4 nm, or about 5 nm to about 8 nm, about 10 nm, about 12 nm, about 15 nm, about 20 nm, about 25 nm, about 30 nm, about 35 nm, about 40 nm, about 50 nm, or about 60 nm. For example, the protective oxide layer 120 has a thickness of about 1 nm to about 60 nm, about 1 nm to about 50 nm, about 1 nm to about 40 nm, about 1 nm to about 35 nm, about 1 nm to about 30 nm, about 1 nm to about 25 nm, about 1 nm to about 20 nm, about 1 nm to about 15 nm, about 1 nm to about 12 nm, about 1 nm to about 10 nm, about 1 nm to about 8 nm, about 1 nm to about 5 nm, about 1 nm to about 3 nm, about 5 nm to about 60 nm, about 5 nm to about 50 nm, about 5 nm to about 40 nm, about 5 nm to about 35 nm, about 5 nm to about 30 nm, about 5 nm to about 25 nm, about 5 nm to about 20 nm, about 5 nm to about 15 nm, about 5 nm to about 12 nm, about 5 nm to about 10 nm, about 5 nm to about 8 nm, about 10 nm to about 60 nm, about 10 nm to about 50 nm, about 10 nm to about 40 nm, about 10 nm to about 35 nm, about 10 nm to about 30 nm, about 10 nm to about 25 nm, about 10 nm to about 20 nm, about 10 nm to about 15 nm, or about 10 nm to about 12 nm.

FIG. 6 depicts a schematic cross-sectional view of the workpiece 100 containing a dielectric layer 130 disposed on the protective oxide layer 120 and covering the second nanopore 402d, according to one or more embodiments described and discussed herein. The dielectric layer 130 can include a spin-on dielectric material or can be deposited or otherwise formed by a vapor deposition process.

In one or more embodiments, the dielectric layer 130 can be, contain, and/or be made from tetraethyl orthosilicate (TEOS) oxide, one or more silane oxides, one or more polyimides, one or more other dielectric materials, or any combination thereof. In one or more examples, the dielectric layer 130 can be or include one or more photo-definable materials, such as a polyimide. For example, the photo-definable material can be made from or include a polymer precursor which is photosensitive, such as a photosensitive polyimide precursor or benzocyclobutene (BCB). In one or more subsequent processes, a desired pattern is exposed directly thereon.

The dielectric layer 130 has a thickness of about 0.5 µm, about 1 µm, about 1.5 µm, or about 2 µm to about 2.5 µm, about 3 µm, about 4 µm, or about 5 µm. For example, the dielectric layer 130 has a thickness of about 0.5 µm to about 5 µm, about 0.5 µm to about 4 µm, about 0.5 µm to about 3 µm, about 0.5 µm to about 2 µm, about 0.5 µm to about 1 µm, about 1 µm to about 5 µm, about 1 µm to about 4 µm, about 1 µm to about 3 µm, about 1 µm to about 2 µm, about 1.5 µm to about 5 µm, about 1.5 µm to about 4 µm, about 1.5 µm to about 3 µm, or about 1.5 µm to about 2 µm.

FIG. 7 depicts a schematic cross-sectional view of the workpiece 100 having a contact hole 136, according to one or more embodiments described and discussed herein. The contact hole 136 extends from within the second silicon layer 108 and completely extends through the second membrane layer 110, the protective oxide layer 120, and the dielectric layer 130. For example, the contact hole 136 can be etched or otherwise formed through the dielectric layer 130, the protective oxide layer 120, the second membrane layer 110, and at least partially into the second silicon layer 108. In some embodiments, the contact hole 136 is etched through the cured polymer of the dielectric layer 130, as well as the other materials of the second silicon layer 108 and completely through the second membrane layer 110, the protective oxide layer 120, using a lithography-etch processing sequence. In one or more embodiments, the contact hole 136 is formed by reactive ion etching (RIE). The diameter of the contact hole 136 can be about 1 µm, about 10 µm, about 50 µm, or about 100 µm to about 250 µm, about 500 µm, about 800 µm, or about 1,000 µm.

Figure 8:
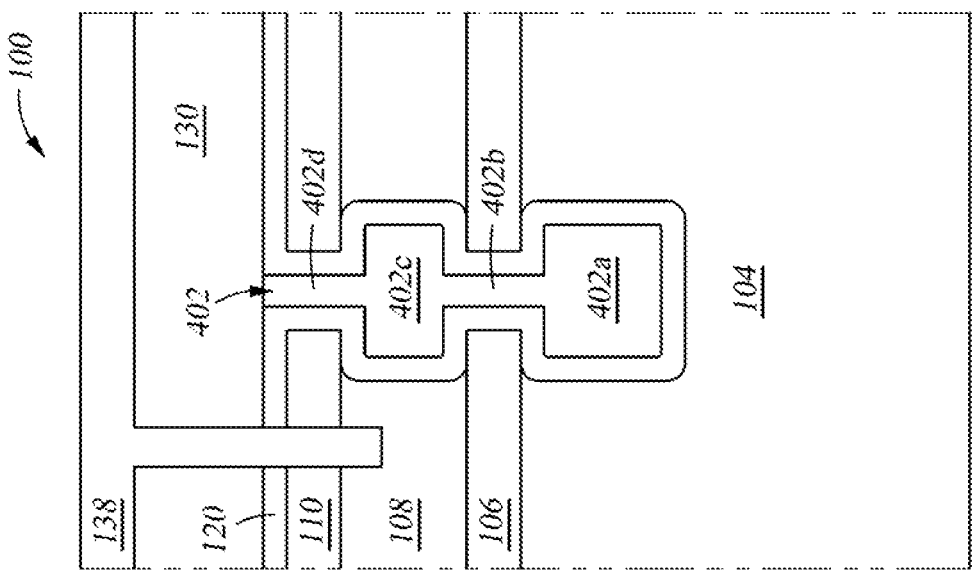
FIG. 8 depicts a schematic cross-sectional view of the workpiece depicted in FIG. 7 after being exposed to a metal deposition process, according to one or more embodiments described and discussed herein.

FIG. 8 depicts a schematic cross-sectional view of the workpiece 100 depicted in FIG. 7 after being exposed to one or more metal deposition processes, according to one or more embodiments described and discussed herein. The workpiece 100 has a metal contact 138 containing one or more conductive materials disposed within the contact hole 136 and across the at least a portion of the upper surface of the dielectric layer 130. The metal contact 138 extends through the dielectric layer 130, the protective oxide layer 120, and the second membrane layer 110, and at least partially into the second silicon layer 108. In one or more aspects, the metal contact 138 extends parallel or substantially parallel to the channel 402, as illustrated in FIG. 8.

The one or more conductive materials disposed in the contact hole 136 forming the metal contact 138 can be or include copper, aluminum, tungsten, titanium, chromium, cobalt, alloys thereof, or any combination thereof. The metal contact 138 can be deposited, plated, or otherwise formed by one or more deposition processes, including electroplating or electrodeposition, electroless deposition, CVD, PE-CVD, PVD, or any combination thereof.

FIG. 9 depicts a schematic cross-sectional view of the workpiece 100 depicted in FIG. 8 after being exposed to one or more etch processes, according to one or more embodiments described and discussed herein. The metal contact 138 disposed on the upper surface of the dielectric layer 130 is a residual layer of the conductive material leftover after the metal contact deposition process. This residual layer containing the conductive material of the metal contact 138 can be etched, polished, and/or otherwise removed to the dielectric layer 130. In some examples, the residual layer containing the conductive material of the metal contact 138 is exposed to a wet etch process, a chemical mechanical process (CMP), an electro-CMP (e-CMP), or any combination thereof.

FIG. 10A depicts a schematic cross-sectional view of the workpiece 100 depicted in FIG. 9 after being exposed to another etch process, and FIG. 10B depicts a schematic top view of the workpiece 100 depicted in FIG. 10A, according to one or more embodiments described and discussed herein. At least a portion of the dielectric layer 130 is etched or otherwise removed to form a well 140 disposed above the channel 402 at the second nanopore 402d, as depicted in FIG. 10A. In some examples, the portion of the dielectric layer 130 is etched with a dry etch process to form the well 140. For example, the well 140 is formed by removing the portion of the dielectric layer 130 with an RIE process or other plasma etch process.

The well 140 can have a diameter of about 0.5 µm, about 1 µm, about 5 µm, about 10 µm, or about 15 µm to about 20 µm, about 30 µm, about 50 µm, about 80 µm, or about 100 µm. For example, the well 140 can have a diameter of about 0.5 µm to about 100 µm, about 0.5 µm to about 90 µm, about 0.5 µm to about 80 µm, about 0.5 µm to about 65 µm, about 0.5 µm to about 50 µm, about 0.5 µm to about 30 µm, about 0.5 µm to about 20 µm, about 0.5 µm to about 10 µm, about 0.5 µm to about 5 µm, about 0.5 µm to about 1 µm, about 10 µm to about 100 µm, about 10 µm to about 90 µm, about 10 µm to about 80 µm, about 10 µm to about 65 µm, about 10 µm to about 50 µm, about 10 µm to about 30 µm, about 10 µm to about 20 µm, or about 10 µm to about 15 µm.

The well 140 can have a depth of about 200 nm, about 300 nm, about 400 nm, or about 450 nm to about 500 nm, about 550 nm, about 600 nm, about 700 nm, about 800 nm, about 1,000 nm, about 2,000 nm, about 3,000 nm, or about 5,000 nm. For example, the well 140 can have a depth of about 200 nm to about 5,000 nm, about 200 nm to about 2,000 nm, about 200 nm to about 1,000 nm, about 200 nm to about 800 nm, about 200 nm to about 600 nm, about 200 nm to about 500 nm, about 200 nm to about 400 nm, about 400 nm to about 5,000 nm, about 400 nm to about 2,000 nm, about 400 nm to about 1,000 nm, about 400 nm to about 800 nm, about 400 nm to about 600 nm, about 400 nm to about 500 nm, about 450 nm to about 500 nm, about 500 nm to about 800 nm, about 500 nm to about 600 nm, or about 500 nm to about 550 nm.

FIG. 11 depicts a schematic cross-sectional view of the workpiece 100 depicted in FIG. 10A after being exposed to another etch process, according to one or more embodiments described and discussed herein. At least a portion of the first silicon layer 104 is etched or otherwise removed to form a well 142 and reveal at least a portion of the protective oxide layer 120 deposited on the inner surfaces of the first reservoir 402a. In one or more examples, the portion of the first silicon layer 104 is etched away with a wet etch process to reveal the portion of the protective oxide layer 120, as depicted in FIG. 11.

Examples of suitable wet etchants used in the wet etching process are aqueous solutions which can be or include one or more of tetramethylammonium hydroxide (TMAH), ammonium hydroxide (NH$_4$OH), hydrazine (N$_2$H$_4$), ethylene diamine and pyrocatechol (EPD), sodium hydroxide (NaOH), potassium hydroxide (KOH), lithium hydroxide (LiOH), or any combination thereof. In one or more examples, the portion of the first silicon layer 104 is removed by exposing the workpiece 100 to an aqueous hydroxide solution (about 30 wt % to about 35 wt % of KOH) at a temperature of about 70° C. to about 90° C. for about 10 hours to about 14 hours.

FIG. 12A depicts a schematic cross-sectional view of the workpiece 100 depicted in FIG. 11A after being exposed to another etch process, and FIG. 12B depicts a schematic top view of the workpiece 100 depicted in FIG. 12A, according to one or more embodiments described and discussed herein. All of substantially all of the protective oxide layer 120 can be etched or otherwise removed, as well as and the lower portion of the dielectric layer 130 disposed in the well 140 can be etched or otherwise removed, as depicted in FIGS. 12A and 12B. Specifically, the protective oxide layer 120 originally deposited on the inner surfaces of the first and second reservoirs 402a, 402c and originally deposited on the inner surfaces of the first and second nanopores 402b, 402d can be etched or otherwise removed by one or more etching process.

In one or more examples, the protective oxide layer 120 and the lower portion of the dielectric layer 130 disposed in the well 140 are etched by one or more wet etch processes. The wet etch process includes exposing the protective oxide layer 120 and the lower portion of the dielectric layer 130 to one or more etching solutions. The etching solution can be or include an aqueous dilute hydrofluoric acid (DHF) solution and/or a buffered aqueous HF solutions, such as an aqueous solution of HF and ammonium fluoride (NH$_4$F). The workpiece 100 is exposed to the etching solution for less than 10 minutes, such as about 1 minute to about 8 minutes.

Each of the first and second nanopores 402b, 402d can independently have diameter $d_3$ of about 0.5 nm, about 1 nm, about 1.25 nm, about 1.5 nm, about 1.75 nm, or about 2 nm to about 2.25 nm, about 2.5 nm, about 2.75 nm, about 3 nm, about 4 nm, about 5 nm, about 6 nm, about 8 nm, about 10 nm, about 15 nm, about 20 nm, about 30 nm, about 40 nm, or about 50 nm. For example, each of the first and second nanopores 402b, 402d can independently have diameter $d_3$ of about 0.5 nm to about 50 nm, about 0.5 nm to about 30 nm, about 0.5 nm to about 20 nm, about 0.5 nm to about 15 nm, about 0.5 nm to about 10 nm, about 0.5 nm to about 8 nm, about 0.5 nm to about 5 nm, about 0.5 nm to about 4 nm, about 0.5 nm to about 3 nm, about 0.5 nm to about 2.5 nm, about 0.5 nm to about 2.25 nm, about 0.5 nm to about 2 nm, about 0.5 nm to about 1.75 nm, about 0.5 nm to about 1.5 nm, about 0.5 nm to about 1.25 nm, about 0.5 nm to about 1 nm, about 0.5 nm to about 0.75 nm, about 1 nm to about 50 nm, about 1 nm to about 40 nm, about 1 nm to about 30 nm, about 1 nm to about 20 nm, about 1 nm to about 15 nm, about 1 nm to about 10 nm, about 1 nm to about 8 nm, about 1 nm to about 5 nm, about 1 nm to about 4 nm, about 1 nm to about 3 nm, about 1 nm to about 2.5 nm, about 1 nm to about 2.25 nm, about 1 nm to about 2 nm, about 1 nm to about 1.75 nm, about 1 nm to about 1.5 nm, about 1 nm to about 1.25 nm, about 1.5 nm to about 50 nm, about 1.5 nm to about 30 nm, about 1.5 nm to about 20 nm, about 1.5 nm to about 10 nm, about 1.5 nm to about 8 nm, about 1.5 nm to about 5 nm, about 1.5 nm to about 4 nm, about 1.5 nm to about 3 nm, about 1.5 nm to about 2.5 nm, about 1.5 nm to about 2 nm, or about 1.5 nm to about 1.75 nm.

In one or more examples, the first membrane layer 106 and the second membrane layer 110 can independently have a thickness of about 0.1 nm to about 40 nm and the first and second nanopores 402b, 402d can independently have diameter $d_3$ of about 0.5 nm to about 50 nm. In other examples, the first membrane layer 106 and the second membrane layer 110 can independently have a thickness of about 0.5 nm to about 20 nm and the first and second nanopores 402b, 402d can independently have diameter $d_3$ of about 1 nm to about 3.5 nm. In some examples, the first membrane layer 106 and the second membrane layer 110 can independently have a thickness of about 0.7 nm to about 10 nm and the first and second nanopores 402b, 402d can independently have diameter $d_3$ of about 1.5 nm to about 2.5 nm. In other examples, the first membrane layer 106 and the second membrane layer 110 can independently have a thickness of about 0.8 nm to about 1.2 nm and the first and second nanopores 402b, 402d can independently have diameter $d_3$ of about 1.75 nm to about 2.25 nm.

In one or more embodiments, the workpiece 100 depicted in FIGS. 12A and 12B is a vertically aligned, dual pore sensor as described and discussed herein, and can be used during sequencing of DNA, RNA, biopolymers, and/or other biomolecules. In the event that either of the first or second nanopores 402b, 402d do not have the desired diameter $d_3$, additional material can be deposited to further reduce the diameter of the first or second nanopores 402b, 402d in order to have a desired diameter $d_3$. Additional details to adjust the diameter of the first or second nanopores 402b, 402d in order to have a desired diameter $d_3$ are further described and discussed below and depicted in FIGS. 13, 14A, and 14B.

FIG. 13 depicts a schematic cross-sectional view of the workpiece 100 depicted in FIG. 12A after being exposed to a deposition process, according to one or more embodiments described and discussed herein. After etching or otherwise removing the protective oxide layer 120 deposited on the inner surfaces of the first and second reservoirs 402a, 402c and the inner surfaces of the first and second nanopores 402b, 402d, the method can also include depositing a spacer layer 150 on at least the inner surfaces of the first and second nanopores 402b, 402d to reduce the diameters therebetween.

For example, the workpiece 100 is exposed to one or more vapor deposition processes to deposit the spacer layer 150 on most, if not all, exposed surfaces on the workpiece 150. The spacer layer 150 is disposed on the exposed surfaces of the first silicon layer 104, the first membrane layer 106, the second silicon layer 108, the second membrane layer 110, the protective oxide layer 120, the dielectric layer 130, and the metal contact 138. The spacer layer 150 disposed on the inner surfaces of the first and second nanopores 402b, 402d (e.g., inner surfaces the first and second membrane layers 106, 110) and the second reservoir 402c (e.g., inner surfaces of the second silicon layer 108). The spacer layer 150 can partially or completely cover or otherwise block the channel 402 at or adjacent the first and/or second nanopores 402b, 402d. The channel 402 is illustrated in FIG. 13 as being completely covered near the first nanopore 402b. In other examples, the spacer layer 150 is conformally or substantially conformally deposited onto the underlying surfaces such that the channel 402 remains completely opened between the wells 140, 142.

The spacer layer 150 includes one or more materials, such as silicon oxide, silicon nitride, silicon oxynitride, dopant variants thereof, or any combination thereof. The spacer layer 150 can be deposited by any vapor deposition process, such as an ALD process, a PE-ALD process, a CVD process, a PE-CVD process, a pulsed-CVD process, or any combination thereof. In one or more examples, the spacer layer 150 can be deposited by an ALD process or a PE-ALD process.

The spacer layer 150 can be deposited to any thickness needed to adjust the diameter of the first or second nanopores 402b, 402d in order to have a desired diameter $d_3$. As such, the spacer layer 150 can have a thickness of about 0.1 nm, about 0.2 nm, about 0.3 nm, about 0.4 nm, about 0.5 nm, about 0.6 nm, about 0.7 nm, about 0.8 nm, about 0.9 nm, about 1 nm, about 1.1 nm, about 1.2 nm, about 1.3 nm, about 1.4 nm, about 1.5 nm, about 1.6 nm, about 1.8 nm, about 2 nm, about 2.5 nm, about 3 nm, about 5 nm, about 7 nm, about 9 nm, about 10 nm, about 15 nm, about 20 nm, or greater. For example, the spacer layer 150 can have a thickness of about 0.1 nm to about 20 nm, about 0.1 nm to about 15 nm, about 0.1 nm to about 10 nm, about 0.1 nm to about 8 nm, about 0.1 nm to about 6 nm, about 0.1 nm to about 5 nm, about 0.1 nm to about 3 nm, about 0.1 nm to about 2 nm, about 0.1 nm to about 1.5 nm, about 0.1 nm to about 1.2 nm, about 0.1 nm to about 1 nm, about 0.1 nm to about 0.8 nm, about 0.1 nm to about 0.6 nm, about 0.1 nm to about 0.5 nm, about 0.1 nm to about 0.3 nm, about 0.5 nm to about 20 nm, about 0.5 nm to about 15 nm, about 0.5 nm to about 10 nm, about 0.5 nm to about 8 nm, about 0.5 nm to about 6 nm, about 0.5 nm to about 5 nm, about 0.5 nm to about 3 nm, about 0.5 nm to about 2 nm, about 0.5 nm to about 1.5 nm, about 0.5 nm to about 1.2 nm, about 0.5 nm to about 1 nm, about 0.5 nm to about 0.8 nm, about 0.5 nm to about 0.6 nm, about 0.8 nm to about 20 nm, about 0.8 nm to about 15 nm, about 0.8 nm to about 10 nm, about 0.8 nm to about 8 nm, about 0.8 nm to about 6 nm, about 0.8 nm to about 5 nm, about 0.8 nm to about 3 nm, about 0.8 nm to about 2 nm, about 0.8 nm to about 1.5 nm, about 0.8 nm to about 1.2 nm, or about 0.8 nm to about 1 nm.

Figure 14B:
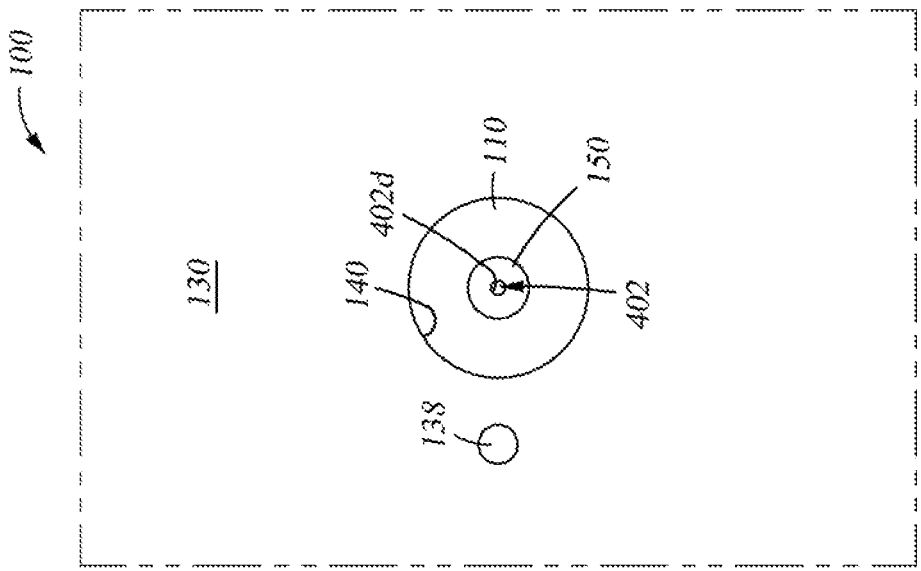
FIG. 14B depicts a schematic top view of the workpiece depicted in FIG. 14A, according to one or more embodiments described and discussed herein.
Figure 14A:
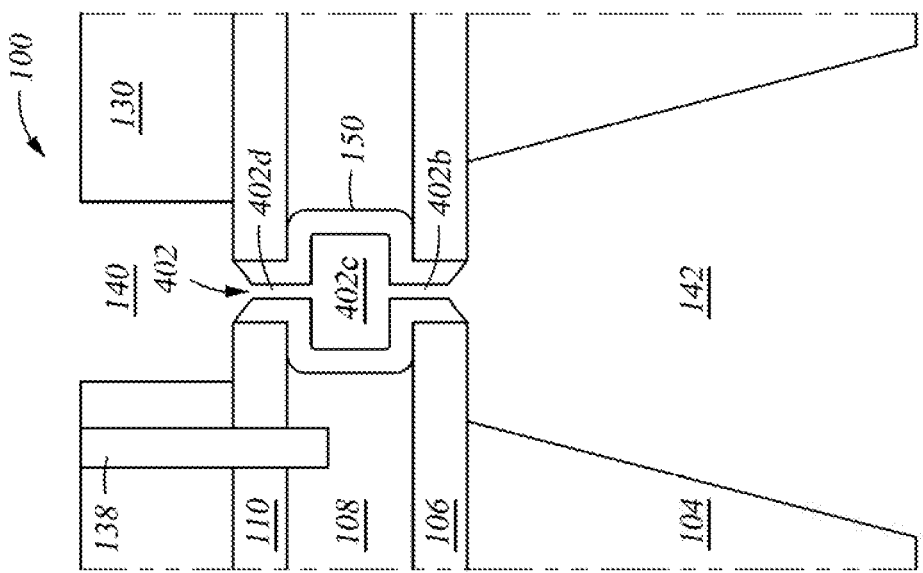
FIG. 14A depicts a schematic cross-sectional view of the workpiece depicted in FIG. 13 after being exposed to another etch process, according to one or more embodiments described and discussed herein.

FIG. 14A depicts a schematic cross-sectional view of the workpiece 100 depicted in FIG. 13 after being exposed to one or more etch processes to remove portions of the spacer layer 150, and FIG. 14B depicts a schematic top view of the workpiece 100, according to one or more embodiments described and discussed herein.

The method includes etching at least a portion of the spacer layer 150 from the upper and side surfaces of the dielectric layer 130 and the upper surface of the metal contact 138. The method also includes etching at least a portion of the spacer layer 150 to produce desired diameter of the channel 402 extending through the first and second nanopores 402b, 402d. As such, the first and second nanopores 402b, 402d have the desired diameter $d_3$. The method further includes etching at least a portion of the spacer layer 150 from a lower surface of the first membrane 106, an upper surface of the second membrane 110, or both surfaces. If the channel 402 is covered or has a block due to the spacer layer 150, the etching process removes enough of the spacer layer 150 to alleviate or completely remove the blockage and free the channel 402.

The overall membrane thicknesses are effectively thinned by etching or otherwise removing at least a portion of the spacer layer 150 from the lower surface of the first membrane 106 and/or the upper surface of the second membrane 110. For example, an overall lower membrane can include the first membrane 106 and the spacer layer 150 disposed on the lower surface of the first membrane 106. The thickness of the overall lower membrane is reduced to a desired thickness by thinning the spacer layer 150 on the lower surface of the first membrane 106 during the etching process. Similarly, an overall upper membrane can include the second membrane 110 and the spacer layer 150 disposed on the upper surface of the second membrane 110. The thickness of the overall upper membrane is reduced to a desired thickness by thinning the spacer layer 150 on the upper surface of the second membrane 110 during the etching process.

In one or more examples, the spacer layer 150 is etched by one or more wet etch processes. The wet etch process includes exposing the spacer layer 150 to one or more etching solutions. The etching solution can be or include an aqueous dilute hydrofluoric acid (DHF) solution and/or a buffered aqueous HF solutions, such as an aqueous solution of HF and ammonium fluoride ($NH_4F$).

Figure 15:
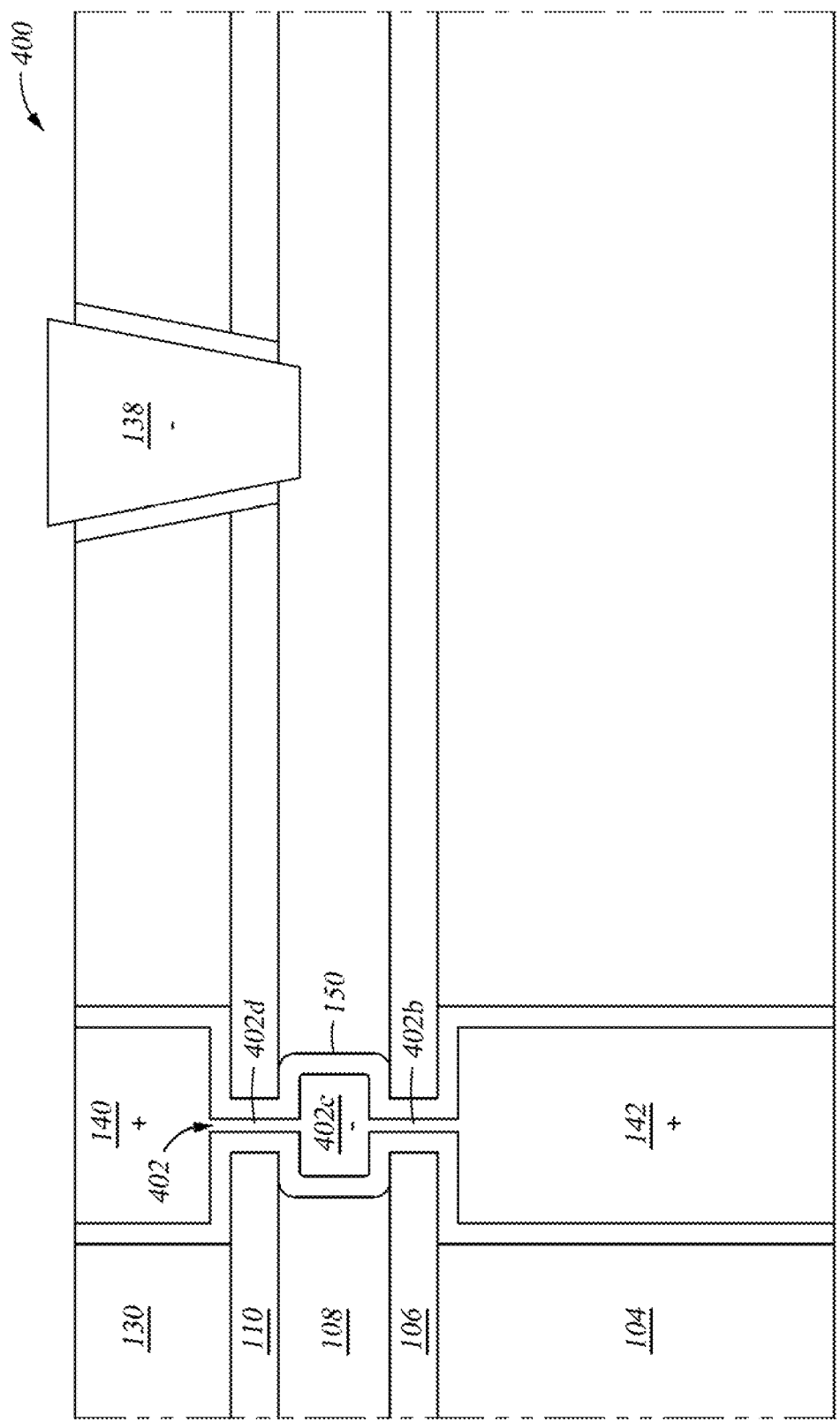
FIG. 15 depicts a schematic cross-sectional view of a dual pore sensor, according to one or more embodiments described and discussed herein.

FIG. 15 depicts a schematic cross-sectional view of a dual pore sensor 400, according to one or more embodiments described and discussed herein. The dual pore sensor 400 is middle grounded at the second reservoir 402c via the metal contact 138 used as an anode. The middle grounding by the second reservoir 402c forms two circuits—an upper circuit via the second nanopore 402d and the well 140 and a lower circuit via the first nanopore 402b and the well 142. Each of the wells 140, 142 independently work as a cathode.

Beneficially, the methods described and discussed herein allow for high volume manufacturing, as well as improvements in quality, repeatability, and manufacturing costs of a vertically aligned, dual pore sensor. Furthermore, the vertically aligned, dual pore sensors described and discussed herein provide better control over biomolecule sequencing of DNA, RNA, and/or other biopolymers over traditional horizontal dual pore systems.

While the foregoing is directed to embodiments of the disclosure, other and further embodiments may be devised without departing from the basic scope thereof, and the scope thereof is determined by the claims that follow. All documents described herein are incorporated by reference herein, including any priority documents and/or testing procedures to the extent they are not inconsistent with this text. As is apparent from the foregoing general description and the specific embodiments, while forms of the present disclosure have been illustrated and described, various modifications can be made without departing from the spirit and scope of the present disclosure. Accordingly, it is not intended that the present disclosure be limited thereby. Likewise, the term "comprising" is considered synonymous with the term "including" for purposes of United States law. Likewise whenever a composition, an element or a group of elements is preceded with the transitional phrase "comprising", it is understood that we also contemplate the same composition or group of elements with transitional phrases "consisting essentially of," "consisting of", "selected from the group of consisting of," or "is" preceding the recitation of the composition, element, or elements and vice versa.

Certain embodiments and features have been described using a set of numerical upper limits and a set of numerical lower limits. It should be appreciated that ranges including the combination of any two values, e.g., the combination of any lower value with any upper value, the combination of any two lower values, and/or the combination of any two upper values are contemplated unless otherwise indicated. Certain lower limits, upper limits and ranges appear in one or more claims below.

The invention claimed is:

1. A method of forming a dual pore sensor, comprising:
   forming a film stack, wherein the film stack comprises:
      a first silicon layer,
      a first membrane layer disposed on the first silicon layer,
      a second silicon layer disposed on the first membrane layer, and
      a second membrane layer disposed on the second silicon layer;
   etching the film stack to produce:
      a first reservoir in the first silicon layer,
      a first nanopore in the first membrane layer,
      a second reservoir in the second silicon layer,
      a second nanopore in the second membrane layer, and
      a channel in fluid communication with the first and second reservoirs and the first and second nanopores;
   depositing a protective oxide layer on the second membrane layer and inner surfaces of the first and second reservoirs and inner surfaces of the first and second nanopores;
   depositing a dielectric layer on the protective oxide layer disposed on the second membrane layer and covering the second nanopore;
   forming a metal contact which extends through the dielectric layer, the protective oxide layer, and the second membrane layer, and at least partially into the second silicon layer;
   etching at least a portion of the dielectric layer to form a well above the second nanopore;
   etching at least a portion of the first silicon layer to reveal at least a portion of the protective oxide layer deposited on the inner surfaces of the first reservoir; and
   etching the protective oxide layer deposited on the inner surfaces of the first and second reservoirs and the inner surfaces of the first and second nanopores.

2. The method of claim 1, wherein the protective oxide layer comprises silicon oxide, a metal oxide, a metal silicate, or any combination thereof.

3. The method of claim 2, wherein the protective oxide layer is deposited by atomic layer deposition.

4. The method of claim 1, wherein each of the first nanopore and the second nanopore independently has a diameter in a range from about 0.5 nm to about 50 nm.

5. The method of claim 1, wherein the dielectric layer comprises a tetraethyl orthosilicate oxide, a silane oxide, a polyimide, or any combination thereof.

6. The method of claim 1, wherein the dielectric layer has a thickness in a range from about 1 µm to about 5 µm.

7. The method of claim 1, wherein forming the metal contact further comprises:
   etching a contact hole through the dielectric layer, the protective oxide layer, and the second membrane layer, and partially into the second silicon layer; and
   depositing a metal into the contact hole to form the metal contact comprising the metal.

8. The method of claim 1, wherein the metal contact extends parallel or substantially parallel to the channel.

9. The method of claim 1, wherein the portion of the dielectric layer is etched with a dry etch process to form the well above the second nanopore, and wherein the portion of the first silicon layer is etched with a wet etch process to reveal the portion of the protective oxide layer deposited on the inner surfaces of the first reservoir.

10. The method of claim 1, wherein the protective oxide layer is etched by a wet etch process.

11. The method of claim 1, further comprising depositing a spacer layer on at least the inner surfaces of the first and second nanopores after etching the protective oxide layer.

12. The method of claim 11, wherein the spacer layer comprises silicon oxide, a silicon nitride, a silicon oxynitride, or any combination thereof.

13. The method of claim 11, wherein the spacer layer is deposited by atomic layer deposition.

14. The method of claim 11, further comprising etching at least a portion of the spacer layer from the inner surfaces of the first and second nanopores within the channel.

15. The method of claim 11, further comprising etching at least a portion of the spacer layer from a lower surface of the first membrane or an upper surface of the second membrane.

16. A method of forming a dual pore sensor, comprising:
   forming a film stack, wherein the film stack comprises:
      a first silicon layer,
      a first membrane layer disposed on the first silicon layer,
      a second silicon layer disposed on the first membrane layer,
      a second membrane layer disposed on the second silicon layer,
      a first reservoir in the first silicon layer,
      a first nanopore in the first membrane layer,
      a second reservoir in the second silicon layer,
      a second nanopore in the second membrane layer, and
      a channel in fluid communication with the first and second reservoirs and the first and second nanopores;

depositing a protective oxide layer on the second membrane layer and inner surfaces of the first and second reservoirs and inner surfaces of the first and second nanopores;

depositing a dielectric layer on the protective oxide layer disposed on the second membrane layer and covering the second nanopore;

forming a metal contact which extends through the dielectric layer, the protective oxide layer, and the second membrane layer, and at least partially into the second silicon layer, wherein the metal contact comprises a metal;

etching at least a portion of the dielectric layer to form a well above the second nanopore;

etching at least a portion of the first silicon layer to reveal at least a portion of the protective oxide layer deposited on the inner surfaces of the first reservoir;

etching the protective oxide layer deposited on the inner surfaces of the first and second reservoirs and the inner surfaces of the first and second nanopores; and depositing a spacer layer on at least the inner surfaces of the first and second nanopores.

17. The method of claim 16, wherein the spacer layer comprises silicon oxide, a silicon nitride, a silicon oxynitride, or any combination thereof, and wherein the spacer layer is deposited by atomic layer deposition.

18. The method of claim 16, further comprising etching at least a portion of the spacer layer from a lower surface of the first membrane or an upper surface of the second membrane.

19. The method of claim 16, wherein each of the first nanopore and the second nanopore independently has a diameter in a range from about 1 nm to about 50 nm.

20. The method of claim 16, wherein the dielectric layer has a thickness in a range from about 1 µm to about 5 µm.

* * * * *